US011473101B2

(12) United States Patent
Leonard et al.

(10) Patent No.: US 11,473,101 B2
(45) Date of Patent: Oct. 18, 2022

(54) METHODS OF IDENTIFYING, SELECTING, AND PRODUCING SOUTHERN CORN RUST RESISTANT CROPS

(71) Applicants: PIONEER HI-BRED INTERNATIONAL, INC., Johnston, IA (US); HENAN AGRICULTURAL UNIVERSITY, Zhengzhou (CN)

(72) Inventors: April L. Leonard, Johnston, IA (US); Jennifer S. Jaqueth, Johnston, IA (US); Shawn Thatcher, Johnston, IA (US); Zhizeng Liu, Johnston, IA (US); Zhaohui Sun, Johnston, IA (US); Bailin Li, Johnston, IA (US); Huimin Li, Zhengzhou (CN); Ce Deng, Zhengzhou (CN); Meng Lv, Zhengzhou (CN); Junqiang Ding, Zhengzhou (CN)

(73) Assignees: Pioneer Hi-Bred International, Inc., Johnston, IA (US); Henan Agricultural University, Zhengzhou (CN)

(*) Notice: Subject to any disclaimer, the term of this patent is extended or adjusted under 35 U.S.C. 154(b) by 0 days.

(21) Appl. No.: 16/814,087

(22) Filed: Mar. 10, 2020

(65) Prior Publication Data
US 2020/0291420 A1 Sep. 17, 2020

(30) Foreign Application Priority Data
Mar. 11, 2019 (WO) ................ PCT/CN2019/077594

(51) Int. Cl.
*C12N 15/82* (2006.01)
*C12Q 1/6895* (2018.01)

(52) U.S. Cl.
CPC ....... *C12N 15/8282* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | | |
|---|---|---|---|---|
| 2008/0172765 A1* | 7/2008 | Katagiri | ............... | C07K 14/415 800/312 |
| 2021/0040569 A1* | 2/2021 | Jaqueth | ................ | C12Q 1/6895 |

FOREIGN PATENT DOCUMENTS

| | | | | |
|---|---|---|---|---|
| WO | WO 2010/083178 | | 7/2010 | |
| WO | WO 2013/098819 | | 7/2013 | |
| WO | WO-2019182884 A1 | * | 9/2019 | ........... C12Q 1/6895 |
| WO | WO 2019/236257 | | 12/2019 | |

OTHER PUBLICATIONS

Bhavani, et al. "Comparative Genomics of the Genomic Region Controlling Resistance to Puccinia Polysora Underw. in *Zea Mays* L.". GSTF International Journal of Biosciences (JBio). 2(2):1-7. (Year: 2013).*
CYMMT; CIMMYTMA 28095, *Zea mays* L. subsp. *mays*, CML 496. (Year: 2006).*
MaizeGDB (B73 RefGen_v2; Zm-B73 Reference NAM 5.0 RefGen_V3). Chr10:2704404..2708671. Published 2013. Obtained from www.maizegdb.org on Jul. 6, 2021. pp. 1.*
Rose et al. "The Maintenance of Extreme Amino Acid Diversity at the Disease Resistance Gene, RPP13, in *Arabidopsis thaliana*". Genetics. 166(3): 1517-1527. (Year: 2003).*
Sun, Gen Bank accession PWZ45972 (Year: 2018).*
CN 106,282,394 A (China Golden Marker (Beijing) Biotech Co Ltd) Jan. 4, 2017 (Jan. 4, 2017) Especially Abstract; p. 2, para 5; p. 5, para 1-2; p. 15, para 10.
AC234175, Gen Bank Accession No. AC234175, *Zea mays* cultivar 873 chromosome 10 clone CH201-352E9, *** Sequencing in Progress•••, 22 unordered pieces, Sep. 13, 2014 [Online]. [Retrieved on Jul. 7, 2020). Retrieved from the internet: <URL: https://www.ncbi.nlm.nih.gov/nuccore/AC234175>) Entire document.
AC198651, GenBank Accession No. AC198651, *Zea mays* cultivar 873 chromosome 10 clone CH201-45H19, Sequencing in Progress, 11 unordered pieces, Sep. 23, 2013 [online], [Retrieved on Jul. 7, 2020). Retrieved from the internet: <URL: https://www.ncbi.nlm.nih.gov/nuccore/AC 198651 >) Entire document.
Xiuping Wang et al: Gene expression profiles in *maize* (L.) leaves inoculation with southern corn rust (*Underw.*), ACTA Physiologiae Plantarum, Springer-Verlag, Berlin/Heidelberg, vol. 34, No. 3, Nov. 24, 2011 (Nov. 24, 2011), pp. 997-1006.
Chunjiang Zhou et al. Characterization and fine mapping of RppQ, a resistance gene to southern corn rust in maize , Molecular Genetics and Genomics, Springer, Berlin, DE, vol. 278, No. 6, Oct. 17, 2007 (Oct. 17, 2007), pp. 723-728.
Ya Zhang et al, Mapping of southern corn rust-resistant genes in the W2D inbred line of maize (*Zea mays* L.)11 , Molecular Breeding, Kluwer Academic Pub Li Shers, DO, vol. 25, No. 3, Oct. 8, 2009 (Oct. 8, 2009), pp. 433-439.
PCT Search Report and Written Opinion prepared for PCT/US2019/032497, completed Jul. 16, 2019.

(Continued)

*Primary Examiner* — Matthew R Keogh
*Assistant Examiner* — David R Byrnes
(74) *Attorney, Agent, or Firm* — Barnes & Thornburg LLP

(57) ABSTRACT

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

8 Claims, No Drawings
Specification includes a Sequence Listing.

(56) References Cited

OTHER PUBLICATIONS

C. X. Chen et al, "Molecular tagging and genetic mapping of the disease resistance gene RppQ to southern corn rust", Theoretical and Applied Genetics; International Journal of Plant Breeding Research, l/ol. 108, No. 5, Nov. 18, 2003 (Nov. 18, 2003), p. 945-950.

Wu Xiaojun et al., "Geographic and genetic identification of RppS, a novel locus conferring broad resistance to southern corn rust disease in China", Jan. 30, 2015 (Jan. 30, 2015), vol. 205, No. 1, p. 17-23.

\* cited by examiner

METHODS OF IDENTIFYING, SELECTING, AND PRODUCING SOUTHERN CORN RUST RESISTANT CROPS

CROSS-REFERENCE TO RELATED APPLICATIONS

This application claims priority to PCT International Application No. PCT/CN2019/077594, filed Mar. 11, 2019, the contents of this application is incorporated by reference in its entirety into the present application.

FIELD

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of RTS21631_Seq_List.txt, a creation date of Feb. 27, 2020, and a size of 24 Kb. The sequence listing filed via EFS-Web is part of the specification and is hereby incorporated in its entirety by reference herein.

BACKGROUND

Corn southern rust (SCR), a fungal disease caused by *Puccinia polysora* Underw., is a major disease in the tropical regions and southern part of the US and China. If SCR reaches the temperate regions (e.g. US Midwest) at critical points in the growing season and if conditions are favorable for rust development, disease intensity can reach epidemic levels very quickly, resulting in severe yield losses. Temperate maize germplasm is in general susceptible to SCR. The identification and utilization of resistance lines and QTL in breeding programs to develop varieties resistance to SCR represent a cost-effective way in controlling SCR. Alternatively, varieties carrying genes responsible to SCR resistance may be developed by transgenic or genome editing technologies. Identification of resistance QTL and genes would accelerate the development of products resistance to SCR. Resistance lines (e.g. Brewbaker, J. L., et al. "General resistance in maize to southern rust (*Puccinia polysora Underw*)." Crop science 51, no. 4 (2011): 1393-1409) or QTL (e.g. Jines, M. P., et al. "Mapping resistance to Southern rust in a tropical by temperate maize recombinant inbred topcross population." Theoretical and Applied Genetics 114, no. 4 (2007): 659-667. Zhang, Y., et al. "Mapping of southern corn rust-resistant genes in the W2D inbred line of maize (*Zea mays* L.)." Molecular breeding 25, no. 3 (2010): 433-439. Zhou C J, et al. (2007) Characterization and fine mapping of RppQ, a resistance gene to southern corn rust in maize. Mol Genet Genomics 278:723-728. Holland, J. B., et al. "Inheritance of resistance to southern corn rust in tropical-by-corn-belt maize populations." Theoretical and Applied Genetics 96, no. 2 (1998): 232-241) have been identified. However, none of the causal genes responsible for SCR resistance have been identified and characterized. There is a continuous need for disease-resistant plants and methods to find disease resistant genes.

SUMMARY

Compositions and methods useful in identifying and selecting plant disease resistance genes, or "R genes," are provided herein. The compositions and methods are useful in selecting disease resistant plants, creating transgenic resistant plants, and/or creating resistant genome edited plants. Plants having newly conferred or enhanced resistance to various plant diseases as compared to control plants are also provided herein. In some embodiments, the compositions and methods are useful in selecting Southern Corn Rust (SCR) disease resistant plants, creating transgenic SCR resistant plants, and/or creating SCR resistant genome edited plants.

An SCR resistant plant may be crossed to a second plant in order to obtain a progeny plant that has the resistant gene allele. The disease resistance may be newly conferred or enhanced relative to a control plant that does not have the favorable allele. The SCR R gene allele may be further refined to a chromosomal interval defined by and including defined markers. In some embodiments, the methods for identifying and/or selecting plants having resistance to SCR are presented. In these methods, DNA of a plant is analyzed for the presence of a resistant gene allele on chromosome 10 that is associated with SCR resistance, wherein said resistant gene allele comprises a "T" at MZA9535-6 (position 186 of reference sequence SEQ ID NO: 18) and an "A" at C06836-1 (position 201 of reference sequence SEQ ID NO: 19), and a plant is identified and/or selected as having SCR resistance if said resistant gene allele is detected. In some embodiments, the methods for identifying and/or selecting plants having resistance to SCR comprise detecting or selecting a genomic region comprising SEQ ID NO: 1. The SCR resistance may be newly conferred or enhanced relative to a control plant that does not have the favorable allele. In a further embodiment, the SCR resistant region comprises a gene encoding an NLR03 polypeptide that confers or enhances resistance to SCR (the "NLR03 gene"). In some embodiments, the NLR03 polypeptide comprises the amino acid sequence as set forth in SEQ ID NO: 2.

In another embodiment, methods of identifying and/or selecting plants with SCR resistance are provided in which one or more marker alleles linked to and associated with any of: a "T" at MZA9535-6 (position 186 of reference sequence SEQ ID NO: 18) and an "A" at C06836-1 (position 201 of reference sequence SEQ ID NO: 19), are detected in a plant, and a plant having the one or more marker alleles is selected. The one or more marker alleles may be linked by 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM or less on a single meiosis based genetic map. The selected plant may be crossed to a second plant to obtain a progeny plant that has one or more marker alleles linked to and associated with any of a "T" at MZA9535-6 (position 186 of reference sequence SEQ ID NO: 18) and an "A" at C06836-1 (position 201 of reference sequence SEQ ID NO: 19).

In another embodiment, methods of introgressing a gene allele associated with SCR resistance are presented herein. In these methods, a population of plants is screened with one or more markers to determine if any of the plants has a gene allele associated with SCR resistance, and at least one plant that has the gene allele associated with SCR resistance is selected from the population. The gene allele comprises a "T" at MZA9535-6 (position 186 of reference sequence SEQ ID NO: 18) and an "A" at C06836-1 (position 201 of reference sequence SEQ ID NO: 19).

In some embodiments, introgression of SCR resistant genes from resistant to susceptible lines may be achieved either by marker-assisted trait introgression, transgenic, or genome editing approaches.

Embodiments include an isolated polynucleotide comprising a nucleotide sequence encoding a NLR03 polypeptide capable of conferring resistance to SCR, wherein the NLR03 polypeptide has an amino acid sequence of at least 50%, at least 75%, at least 80%, at least 85%, at least 90%, at least 95% identity, at least 96% identity, at least 97% identity, at least 98% identity, or at least 99% identity when compared to SEQ ID NO: 2. In another embodiment, an isolated polynucleotide comprises a nucleotide sequence encoding a NLR03 polypeptide capable of conferring resistance to SCR, wherein the NLR03 polypeptide has an amino acid sequence of at least 50%, at least 75%, at least 80%, at least 85%, at least 90%, and at least 95% identity, when compared to SEQ ID NO: 2.

Additional embodiments of the present disclosure include a vector comprising a polynucleotide of the disclosure, such as SEQ ID NO: 1, or a recombinant DNA construct comprising a polynucleotide disclosed herein operably linked to at least one regulatory sequence. A plant cell, as well as a plant, each comprising the recombinant DNA construct of an embodiment disclosed herein, and a seed comprising the recombinant DNA construct are also embodied.

In some embodiments, the compositions and methods relate to a modified plant having increased resistance to a disease, wherein the allele causing the increased disease resistance comprises a nucleotide sequence encoding a NLR03 resistance gene, wherein the NLR03 resistance gene is at least 50%, at least 75%, at least 80%, at least 85%, at least 90%, and at least 95% identity, at least 96% identity, at least 97% identity, at least 98% identity, or at least 99% identity to the sequence set forth in SEQ ID NO: 2.

The methods embodied by the present disclosure relate to a method for transforming a host cell, including a plant cell, comprising transforming the host cell with the polynucleotide of an embodiment of the present disclosure; a method for producing a plant comprising transforming a plant cell with the recombinant DNA construct of an embodiment of the present disclosure and regenerating a plant from the transformed plant cell, and methods of conferring or enhancing disease resistance, comprising transforming a plant with the recombinant DNA construct disclosed herein.

In one embodiment a method of altering the level of expression of a protein capable of conferring disease resistance in a plant or plant cell is provided wherein the method comprises (a) transforming a plant cell with a recombinant DNA construct disclosed herein and (b) growing the transformed plant cell under conditions that are suitable for expression of the recombinant DNA construct wherein expression of the recombinant DNA construct results in production of altered levels of a protein capable of conferring disease resistance in the transformed host.

Plants identified and/or selected using any of the methods presented above are also provided.

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The NBS-LRR ("NLR") group of R-genes is the largest class of R-genes discovered to date. In *Arabidopsis thaliana*, over 150 are predicted to be present in the genome (Meyers, et al., (2003), Plant Cell, 15:809-834; Monosi, et al., (2004), Theoretical and Applied Genetics, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) Genome Research, 12:1871-1884; Monosi, (2004) supra; Pan, et al., (2000), Journal of Molecular Evolution, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), Current Biology: CB, 8:R226-R227). The LRR region appears to be the region that interacts with the pathogen AVR products (Michelmore, et al., (1998), Genome Res., 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), Genome Research, 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

An allele is "associated with" a trait when it is part of or linked to a DNA sequence, or is an allele that affects the expression of the trait. The presence of the allele is an indicator of how the trait will be expressed.

As used to herein, "disease resistant" or "have resistance to a disease" refers to a plant showing increase resistance to a disease compared to a control plant. Disease resistance may manifest in fewer and/or smaller lesions, increased plant health, increased yield, increased root mass, increased plant vigor, less or no discoloration, increased growth, reduced necrotic area, or reduced wilting. In some embodiments, an allele may show resistance to one or more diseases.

Diseases affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; aspergillus ear and kernel rot; banded leaf and sheath spot; black bundle disease; black kernel rot; borde blanco; brown spot; black spot; stalk rot; cephalosporium kernel rot; charcoal rot; corticium ear rot; curvularia leaf spot; didymella leaf spot; diplodia ear rot and stalk rot; diplodia ear rot; seed rot; corn seedling blight; diplodia leaf spot or leaf streak; downy mildews; brown stripe downy mildew; crazy top downy mildew; green ear downy mildew; graminicola downy mildew; java downy mildew; philippine downy mildew; sorghum downy mildew; spontaneum downy mildew; sugarcane downy mildew; dry ear rot; ergot; horse's tooth; corn eyespot; fusarium ear and stalk rot; fusarium blight; seedling root rot; gibberella ear and stalk rot; gray ear rot; gray leaf spot; cercospora leaf spot; helminthosporium root rot; hormodendrum ear rot; cladosporium rot; hyalothyridium leaf spot; late wilt; northern leaf blight; white blast; crown stalk rot; corn stripe; northern leaf spot; helminthosporium ear rot; penicillium ear rot; corn blue eye; blue mold; phaeocytostroma stalk rot and root rot; phaeosphaeria leaf spot; physalospora ear rot; botryosphaeria ear rot; pyrenochaeta stalk rot and root rot; pythium root rot; pythium stalk rot; red kernel disease; rhizoctonia ear rot; sclerotial rot; rhizoctonia root rot and stalk rot; rostratum leaf spot; common corn rust; southern corn rust; tropical corn rust; sclerotium ear rot; southern blight; selenophoma leaf spot; sheath rot; shuck rot; silage mold; common smut; false smut; head smut; southern corn leaf blight and stalk rot; southern leaf spot; tar spot; trichoderma ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ringspot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cereal mosaic.

Diseases affecting plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; alternaria leaf spot; and stem rot.

Disease affecting soybean plants include, but are not limited to, alternaria leaf spot; anthracnose; black leaf blight; black root rot; brown spot; brown stem rot; charcoal rot; choanephora leaf blight; downy mildew; drechslera blight; frogeye leaf spot; leptosphaerulina leaf spot; mycoleptodiscus root rot; neocosmospora stem rot; phomopsis seed decay; phytophthora root and stem rot; phyllosticta leaf spot; phymatotrichum root rot; pod and stem blight; powdery mildew; purple seed stain; pyrenochaeta leaf spot; pythium rot; red crown rot; dactuliophora leaf spot; rhizoctonia aerial blight; rhizoctonia root and stem rot; rust; scab; sclerotinia stem rot; sclerotium blight; stem canker; stemphylium leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; alternaria black spot; anthracnose; black leg; black mold rot; black root; brown girdling root rot; cercospora leaf spot; clubroot; downy mildew; fusarium wilt; gray mold; head rot; leaf spot; light leaf spot; pod rot; powdery mildew; ring spot; root rot; sclerotinia stem rot; seed rot, damping-off; root gall smut; southern blight; verticillium wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; erwinia stalk rot and head rot; lternaria leaf blight, stem spot and head rot; botrytis head rot; charcoal rot; downy mildew; fusarium stalk rot; fusarium wilt; myrothecium leaf and stem spot; phialophora yellows; phoma black stem; phomopsis brown stem canker; phymatotrichum root rot; phytophthora stem rot; powdery mildew; pythium seedling blight and root rot; rhizoctonia seedling blight; rhizopus head rot; sunflower rust; sclerotium basal stalk and root rot; septoria leaf spot; verticillium wilt; white rust; yellow rust; dagger; pin; lesion; reniform; root knot; and chlorotic mottle;

Disease affecting sorghum plants include, but are not limited to, bacterial leaf spot; bacterial leaf streak; bacterial leaf stripe; acremonium wilt; anthracnose; charcoal rot; crazy top downy mildew; damping-off and seed rot; ergot; fusarium head blight, root and stalk rot; grain storage mold; gray leaf spot; latter leaf spot; leaf blight; milo disease; oval leaf spot; pokkah boeng; pythium root rot; rough leaf spot; rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to southern corn rust). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) Corn and corn improvement). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. Offspring comprising the desired allele may be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA).

Depending on the DNA marker technology, the marker may consist of complementary primers flanking the locus and/or complementary probes that hybridize to polymorphic alleles at the locus. A DNA marker, or a genetic marker, may also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

Genetic Mapping

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," Nat Genet 7:180-184; Hastbacka et al. (1992) "Linkage disequilibrium mapping in isolated founder populations: diastrophic dysplasia in Finland," Nat Genet 2:204-211; Kerem et al. (1989) "Identification of the cystic fibrosis gene: genetic analysis," Science 245:1073-1080) and maize (Remington et al., (2001) "Structure of linkage disequilibrium and phenotype associations in the maize genome," Proc Natl Acad Sci USA 98:11479-11484; Thornsberry et al. (2001) "Dwarf8 polymorphisms associate with variation in flowering time," Nat Genet 28:286-289; reviewed by Flint-Garcia et al. (2003) "Structure of linkage disequilibrium in plants," Annu Rev Plant Biol. 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," Nat Rev Genet 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," Annu Rev Plant Biol. 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant co-segregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Chromosomal Intervals

Chromosomal intervals that correlate with the disease resistance trait are provided. A variety of methods are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for a disease resistance trait.

Conversely, e.g., if two markers in close proximity show co-segregation with the desired phenotypic trait, it is sometimes unclear if each of those markers identify the same gene or two different gene or multiple genes. Regardless, knowledge of how many genes are in a particular physical/genomic interval is not necessary to make or practice that which is presented in the current disclosure.

The chromosome 10 interval may encompass any of the markers identified herein as being associated with the SCR resistance trait including a "T" at MZA9535-6 (position 186 of reference sequence SEQ ID NO: 18) and an "A" at C06836-1 (position 201 of reference sequence SEQ ID NO: 19). Any marker located within these intervals can find use as a marker for SCR resistance and can be used in the context of the methods presented herein to identify and/or select plants that have resistance to SCR, whether it is newly conferred or enhanced compared to a control plant. In certain embodiments, markers located upstream and downstream of NLR03 gene position are very tightly linked genetically and physically and hence may be used to select the NLR03 gene for trait introgression and products development.

Chromosomal intervals can also be defined by markers that are linked to (show linkage disequilibrium with) a disease resistant gene, and $r^2$ is a common measure of linkage disequilibrium (LD) in the context of association studies. If the $r^2$ value of LD between a chromosome 7 marker locus in an interval of interest and another chromosome 7 marker locus in close proximity is greater than ⅓ (Ardlie et al., Nature Reviews Genetics 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) could also be used to predict disease resistance in a plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele "T" for a specific line or variety with disease resistance, but the allele 'T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms makes this process highly efficient and effective.

Many of the markers presented herein can readily be used as single nucleotide polymorphic (SNP) markers to select for the NLR03 gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the SCR disease resistance trait. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with SCR disease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with SCR disease resistance. For example, a SNP haplotype at the a "T" at MZA9535-6 (position 186 of reference sequence SEQ ID NO: 18) and an "A" at C06836-1 (position 201 of reference sequence SEQ ID NO: 19), or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Plants identified, modified, and/or selected by any of the methods described above are also of interest.

Proteins and Variants and Fragments Thereof

NLR03 polypeptides are encompassed by the disclosure. "NLR03 polypeptide" and "NLR03 protein" as used herein interchangeably refers to a polypeptide(s) having SCR resistance activity, and is sufficiently identical to the NLR03 polypeptide of SEQ ID NO: 2. A variety of NLR03 polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full length sequence of a polypeptide. The term "about" when used herein in context with percent sequence identity means+/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to an NLR03 polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments a NLR03 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of SEQ ID NO: 2, wherein the NLR03 polypeptide has SCR resistance when expressed in a plant.

Methods for such manipulations are generally known in the art. For example, amino acid sequence variants of a NLR03 polypeptide may be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of an NLR03 polypeptide to confer disease resistance may be improved by the use of such techniques upon the compositions of this disclosure.

Nucleic Acid Molecules and Variants and Fragments Thereof

Isolated or recombinant nucleic acid molecules comprising nucleic acid sequences encoding NLR03 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding NLR03 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding NLR03 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an NLR03 polypeptide is a non-genomic sequence.

A variety of polynucleotides that encode NLR03 polypeptides or related proteins are contemplated. Such polynucleotides are useful for production of NLR03 K polypeptides in host cells when operably linked to a suitable promoter, transcription termination and/or polyadenylation sequences. Such polynucleotides are also useful as probes for isolating homologous or substantially homologous polynucleotides that encode NLR03 polypeptides or related proteins.

In some embodiments the nucleic acid molecule encoding an NLR03 polypeptide is a polynucleotide having the sequence set forth in SEQ ID NO: 2, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the NLR03 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an NLR03 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 2, wherein the NLR03 polypeptide has SCR resistance activity when expressed in a plant.

In some embodiments the nucleic acid molecule encodes an NLR03 polypeptide variant comprising one or more amino acid substitutions to the amino acid sequence of SEQ ID NO: 2.

Nucleic acid molecules that are fragments of these nucleic acid sequences encoding NLR03 polypeptides are also encompassed by the embodiments. "Fragment" as used herein refers to a portion of the nucleic acid sequence encoding an NLR03 polypeptide. A fragment of a nucleic acid sequence may encode a biologically active portion of an NLR03 polypeptide or it may be a fragment that can be used as a hybridization probe or PCR primer using methods disclosed below. Nucleic acid molecules that are fragments of a nucleic acid sequence encoding an NLR03 polypeptide comprise at least about 150, 180, 210, 240, 270, 300, 330, 360, 400, 450, or 500 contiguous nucleotides or up to the number of nucleotides present in a full-length nucleic acid sequence encoding a NLR03 polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the NLR03 polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length NLR03 polypeptide as set forth in SEQ ID NO: 2.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a NLR03 polynucleotide encodes a NLR03 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

The embodiments also encompass nucleic acid molecules encoding NLR03 polypeptide variants. "Variants" of NLR03 polypeptide encoding nucleic acid sequences include those sequences that encode the NLR03 polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the NLR03 polypeptides disclosed herein.

The skilled artisan will further appreciate that changes can be introduced by mutation of the nucleic acid sequences thereby leading to changes in the amino acid sequence of the encoded NLR03 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are disclosed in Sambrook and Russell, (2001), *supra*.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and/or a regulatory sequence and a second sequence, wherein the promoter and/or regulatory sequence initiates, mediates, and/or affects transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter or regulatory sequence may be the natural sequence or alternatively a synthetic sequence. The term "foreign" as used herein indicates that the promoter is not found in the native organism into which the promoter is introduced. As used herein, the term "heterologous" in reference to a sequence means a sequence that originates from a foreign species or, if from the same species, is substantially modified from its native form in composition and/or genomic locus by deliberate human intervention. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an NLR03 polypeptide of the embodiments. In some embodiments the DNA construct comprises a polynucleotide encoding a fusion protein comprising an NLR03 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers include, for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants include, but are not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) EMBO J. 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods,* ed. Gamborg and Phillips, (Springer-Verlag, Berlin) and McCabe, et al., (1988) *Bio/technology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues,* ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

Methods to Introduce Genome Editing Technologies into Plants

In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENs, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an SCR resistance NLR03 gene allele has been identified in a genome, genome editing technologies may be used to alter or modify the polynucleotide sequence. Site specific modifications that can be introduced into the desired NLR03 gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the NLR03 polynucleotide compositions within the genome of a plant, in order to generate molecular stacks disease resistant proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. QTL Mapping

Southern corn rust (SCR), caused by the biotrophic pathogen *Puccinia polysora*, is a major disease in many maize-growing regions. A SCR resistant inbred line was crossed to PH11VR, a SCR susceptible inbred line, to generate F1s. The F1 was used to create a doubled haploid population for the initial QTL discovery. 149 F1 double haploid lines were phenotyped for SCR resistance. The severity of SCR is rated by visual inspection 2-4 weeks after flowering, using a nine-point scale, with 1 being highly susceptible and 9 being the most resistant. Scores between 1-3 are considered susceptible with a score of "2" representing 80% leaf loss. Scores between 4-6 are considered intermediate with a score of "5" representing 35% leaf loss. Scores of 7-9 are considered resistant with a score of "8" representing 5% leaf loss. The phenotypic scores within this population ranged from 2 to 8, with an average score of 5.2. 127 of the double haplotype lines were genotyped with 243 SNP markers located across the whole genome. QTL mapping was performed with WinQTLCartographer using Composite Interval Mapping analysis. A QTL was discovered on chromosome 10 with a peak at marker C01957-1 (LOD score of 14.4), flanked by markers C00429-801 and C002DC9-001. The phenotypic variation explained (PVE %) was 37.57%, as calculated using ICIMapping software version 3.2.

Example 2. QTL Fine Mapping and Candidate Gene Identification

To fine map the resistance gene, the F1 was backcrossed to the susceptible parent PH11VR, followed by more backcrosses and selfing to generate the BC2F2 and BC3F3 mapping populations. Approximately 1000 BC2F2 and 750 BC3F3 individuals were genotyped with SNP markers flanking the QTL interval to select recombinant individuals. Recombinants from the ~1750 individuals were self-pollinated. Fixed recombinants were generated and phenotyped. Additional SNP markers within the QTL interval were developed and used to genotype the recombinants. Using this approach, the interval was narrowed to a 411,630 bp region on Chr10 between 2,345,245 and 2,756,875 (B73 v4 positions), between markers SCR_11 (SEQ ID NOs: 3 and 4; See Table 1). An additional 1500 F2s and 1100 BC1F1s derived from the SCR resistant line and PH11VR were used to further narrow down the QTL interval, with the same approach as described before. Finally, the QTL was delimited to a 113,504 bp interval on Chr10 between 2,643,669 and 2,757,139 (B73 v4 positions), flanked by markers SCR_2780626 (SEQ ID NOs: 5-7; See Table 1).

To identify the candidate resistance gene within the interval, a BAC library was generated from the inbred line PH7WC. PH7WC is a parent of the SCR resistant line and the two lines are identical in the QTL region. The BAC library was screened using probes designed within the fine-mapped region and positive BACs were selected for PacBio sequencing. The sequenced BACs assembled into two contigs. Using Fgensh gene prediction analysis, three NLRs (NLR01, NLR02 and NLR03) were identified within the assembled contigs. Transgenic plants expression each of these genes (using genomic fragments including the promoter region) are generated and tested for efficacy against the SCR pathogen. NLR03 (SEQ ID NO: 2) is expected shown to confer resistance, while the other two NLRs are not.

Example 3. QTL Mapping in CML496

CML496, an inbred line resistant to SCR, was crossed with a susceptible line, Lx9801. The F1 progeny from this cross was then backcrossed to Lx9801 to create a BC1F1 population. CML496 (30 individuals), Lx9801 (30 individuals), the F1 progeny (30 individuals), and the BC1F1 population (100 individuals) were phenotyped for SCR resistance. Disease severity was assessed at 30 days post-pollination using a scale from 1 (the most resistant phenotype) to 9 (the most susceptible phenotype). The average scores of CML496 and Lx9801 were 1.0 and 8.5, respectively, and the F1 plants were highly resistant to SCR with an average score of 1.5. For the BC1F1 population, there were 36 highly resistant plants with SCR scores of 1 or 2, and 46 highly susceptible plants with SCR scores of 8 or 9. The 18 remaining plants showed an intermediate level of resistance with scores ranging from 3 to 7. The 36 resistant plants and 46 susceptible plants from the BC1F1 population were used to map the resistance QTL from CML496 (RppCML496). SSR marker on chromosome 10 (bins 10.00, 10.01, and 10.02) were selected to genotype the BC1F1 population. A resistance QTL, RppCML496, was identified and flanked by the SSR markers umc1380 (SEQ ID NOs: 14 and 15) and umc2053 (SEQ ID NOs: 16 and 17; See Table 2).

TABLE 1

Primers and Probes for Markers for QTL Mapping

| Marker Name | Forward Primer (5'-3') | Reverse Primer (5'-3') | Probe | Type | Resistant | Susceptible | B73v4 SNP Position |
|---|---|---|---|---|---|---|---|
| SCR_11 | SEQ ID NO: 3 | SEQ ID NO: 4 | | InDel Marker | | | |
| SCR_2839516 | SEQ ID NO: 5 | SEQ ID NO: 6 | SEQ ID NO: 7 | KASP Marker | C | T | 2756854 |
| SCR_2780626 | SEQ ID NO: 8 | SEQ ID NO: 9 | SEQ ID NO: 10 | KASP Marker | G | C | 2643669 |
| SCR_2839801 | SEQ ID NO: 11 | SEQ ID NO: 12 | SEQ ID NO: 13 | KASP Marker | G | C | 2757138 |

TABLE 2

NLR03 QTL and Fine Mapping Markers

| Marker Name | Forward Primer (5'-3') | Reverse Primer (5'-3') | Probe | Marker Type | B73 v4 Position | B73v4 SNP Position | Resistant | Susceptible |
|---|---|---|---|---|---|---|---|---|
| umc1380_For | SEQ ID NO: 14 | SEQ ID NO: 15 | | SSR Marker | 1810080-1809953 | | | |
| umc2053_For | SEQ ID NO: 16 | SEQ ID NO: 17 | | SSR Marker | 4297766-4297689 | | | |
| SCR_2636645 | SEQ ID NO: 20 | SEQ ID NO: 21 | SEQ ID NO: 22 | KASP Marker | 2561572-2561594 | 2561694 | G | A |
| SCR_2839039 | SEQ ID NO: 23 | SEQ ID NO: 24 | SEQ ID NO: 25 | KASP Marker | 2756352-2756377 | 2756377 | A | T |
| InDel2752077 | SEQ ID NO: 26 | SEQ ID NO: 27 | | InDel | 2751932-2752131 | | | |

Example 4. QTL Fine Mapping and Candidate Gene Identification in CML496

An F2 population of 2,944 individuals were used to fine map RppCML496. 237 recombinants were identified by genotyping with flanking markers MZA9535-6 (SEQ ID NO: 18) and C06836-1 (SEQ ID NO: 19; See Table 3). These recombinants were selfed and progeny used to determine SCR resistance. Additional SNP markers within the QTL interval were developed and used to genotype the recombinants. The QTL interval was narrowed down to ~195 kb on chromosome 10 between 2,561,594 bp and 2,839,039 bp (B73 v4) using the markers SCR_2636645 (SEQ ID NOs: 20-22; See Table 2). To identify the causal gene for SCR resistance, whole genome sequence for CML496 was generated by PacBio sequencing. The size of the QTL interval, ~195 kb based on B73 v4, is approximately 650 kb in CML496. With information from the CML496 sequence, an additional marker, InDel2752077 (SEQ ID NOs: 26 and 27; See Table 2), was developed which further delimited the QTL interval to approximately 137 kb in the CML496 genome. There is only one annotated NLR gene in the interval. This NLR was 100% identical to NLR03 in the SCR resistant line of Example 1, the candidate gene in the SCR QTL interval. Transgenic plants expression this NLR gene (using the genomic fragment including the promoter region) were generated and tested for efficacy against the SCR pathogen.

TABLE 3

NLR03 Haplotype Markers

| Marker Name | Reference Sequence | B73 v4 Position | B73v4 SNP Position | Resistant | Susceptible |
|---|---|---|---|---|---|
| MZA9535-6 | SEQ ID NO: 18 | 2364320-2364750 | 2364505 | T | A |
| C06836-1 | SEQ ID NO: 19 | 3616302-3616702 | 3616502 | A | G |

TABLE 4

NLR03 Sequences

| SEQ ID NO: | Description of SEQ ID NO: |
|---|---|
| 1 | NLR03 CDS |
| 2 | NLR03 Aminoi Acid Sequence |

Example 5. Transgenic Validation of NLR03 as the Causal Gene

Genomic sequence of the NLR03 gene (including the promoter region) was synthesized and cloned into a binary vector for transformation in ED85E. Six single copy quality events were selfed to generate 1:2:1 segregating T1 seed. For one event, plants were backcrossed to the progenitor to produce 1:1 segregating seed. Resulting T1 plants were inoculated with the *Puccinia polysora* urediospores and kept in the greenhouse for 10 days. Greenhouse disease scoring was done visually as susceptible (score=1) or resistant (Score=5) based on high or low level of sporulation, respectively. The test included 28 T1 plants with a single or double copy of transgene and 17 T1 plants without the transgene; a total of 7 events were tested. Of the 28 transgene positive plants, 23 were resistant and of the 17 null plants, 15 were susceptible; on the average the null plants were more susceptible (score=1.5) than plants with the transgene (score=4.3).

The invention claimed is:

1. A recombinant DNA construct comprising a polynucleotide operably linked to at least one heterologous regulatory sequence wherein said polynucleotide comprises a nucleic acid sequence encoding an amino acid sequence having at least 95% sequence identity to SEQ ID NO: 2.

2. The recombinant DNA construct of claim 1, wherein said at least one heterologous regulatory sequence is a promoter functional in a plant cell.

3. The recombinant DNA construct of claim 1, wherein the polynucleotide comprises a nucleic acid sequence having at least 95% sequence identity to SEQ ID NO: 1.

4. A transgenic plant cell comprising the recombinant DNA construct of claim 1.

5. A transgenic plant comprising the transgenic plant cell of claim 4.

6. The transgenic plant of claim 5, wherein said transgenic plant is selected from the group consisting of: *Arabidopsis*, maize, soybean, sunflower, sorghum, canola, wheat, alfalfa, cotton, rice, barley, millet, sugar cane, and switchgrass.

7. Transgenic seed produced from the transgenic plant of claim 5, wherein cells of said seed comprise a recombinant polynucleotide operably linked to at least one heterologous regulatory sequence wherein said polynucleotide comprises a nucleic acid sequence encoding an amino acid sequence having at least 95% sequence identity to SEQ ID NO: 2.

8. A progeny plant derived from the transgenic plant of claim 5, wherein said progeny plant comprises in its genome a recombinant polynucleotide operably linked to at least one heterologous regulatory sequence wherein said polynucleotide comprises a nucleic acid sequence encoding an amino acid sequence having at least 95% sequence identity to SEQ ID NO: 2.

* * * * *

SEQUENCE LISTING

<160> NUMBER OF SEQ ID NOS: 27

<210> SEQ ID NO 1
<211> LENGTH: 4269
<212> TYPE: DNA
<213> ORGANISM: Zea mays

<400> SEQUENCE: 1

-continued

| | |
|---|---|
| atggaggtgg ctctgggaac ggccaagtct ctccttggcc atgttctcaa cagtatctcc | 60 |
| gacgactgga tgaaatccta cgtgtccagc gccgagctcg gcaccaacct taacatgatc | 120 |
| aaagagaaga tgcggtacgc tagagcgctg ctggacgtgg ccaaggggag ggatgacgtc | 180 |
| gtcgccggga accccaacct gctggagcag ctcgagactc tcggcaagaa ggtcgacgag | 240 |
| gctgaggatg ctgtggacga gcttcactac ttcatgatcc aggacaaaca cgacgggact | 300 |
| cgagacgccg caccggagtt gggcggtggc ctcgcagccc aagctcacca tgcccgccat | 360 |
| gctgctcgcc acactgctgg taactggctc tcatgcttct ctggctgctg tacccgagac | 420 |
| aatgctgctg ctaccgatgc catgtctggt gacggtggcc atgttggaaa gttgtcattc | 480 |
| aatcgagtgg ctatgtccaa caaaatcaag ctcctcatag aggagctgca atccaactct | 540 |
| actcctgtct ctgacttgct caagatagtg tcagacacaa ccaactttag ctcctccact | 600 |
| aaaaggcccc cgacaagctc tcaaatcaca caggacaagt tgtttgggag gatgccatc | 660 |
| tttaaaaaaa ctatagatga tattatcata gccaaagata gtggcaaaac cttgtctgtt | 720 |
| cttcctatat ttggcctagg gggcattggg aagactacct tcacccagca cctatacaat | 780 |
| cacacagagt ttgaaaaata tttcactgtt agggtctgga tatgtgtatc gactaatttt | 840 |
| gatgtgctta ggctcaccaa agagatcctg agctgcctac ccgcaactga aaatgcagga | 900 |
| gataaaatag caaatgacac aaccaacttt gacctgcttc agaaatccat cgcagagagg | 960 |
| ttgaaatcca aaaggtttct gattgtcttg gatgacatat gggaatgcag caataatgag | 1020 |
| gagtgggaga actagtagc tccatttaaa aagaatgata ccagtggcaa catgattctt | 1080 |
| gtcacaaccc gattcccgaa aattgtagat ttggtgaaaa agaaactaa cccagttgac | 1140 |
| cttcgcggtt tggatcctga tgagttctgg aaattcttcc agatatgtgc atttggtagt | 1200 |
| attcaagatg ttgagcatgg tgatcaagag ttaattggta ttgcaagaca aatagcagat | 1260 |
| aagctaaaat gctccccact tgcagccaaa acagttggtc ggctattgat taagaaaccc | 1320 |
| cttcaggaac attggatgaa aattcttgag aacaaacagt ggctagagga aaaaatggc | 1380 |
| gatgatatta tcccagcctt gcaaattagc tatgactacc ttcccttcca tctgaaaaaa | 1440 |
| tgtttttcat cttttgccct tttccctgag gattataaat tgataagtc tgagattatt | 1500 |
| cgtttatggg attcaatagg aatcataggt tctagtatac agcaaaagaa aatagaggac | 1560 |
| ataggatcga attattttga tgaactatta gatagttgtt ttcttataaa aggggaaaat | 1620 |
| gattttatg taatgcatga tttaatcctt gatctttcac ggactgtttc aaaacaagat | 1680 |
| tgtgcctata tcgattgttc tagttttgag gcaaataaca tcccacagtc tatccgttac | 1740 |
| ctatccattt ccatgcataa tcattgtgct cagaatttcg aggaagaaat ggctaaactg | 1800 |
| aaggaaagga tagacattaa aaatttgcgg ggtttgatga tatttggaaa ctacattagg | 1860 |
| ttacaactgg tcaatatttt aagggacaca tttaaggaaa taagacgtct tcgtgttcta | 1920 |
| tctatattta tactcccca tagttccttg ccaaacaact tttcagagct tatccatctt | 1980 |
| cgctacttaa aactcaattc accttcttac ttagaaatat ctttgccaaa cacaatctca | 2040 |
| aggttttatc acctgaaatt tctagatctt aaacaatggg gaagtgatcg ttctttgcct | 2100 |
| aaggacatta gccgccttga aaatctacgc catttcattg cttcaaaaga gtttcatacc | 2160 |
| aatgttcctg aggtggggaa aatgaaattt ttacaagaac tgaaagaatt ccatgttaag | 2220 |
| aaagagagtg ttggatttga gctaggagag ttggggaaac tagcagagct tggaggggag | 2280 |
| ctcaatatac ttgggcttga aaaggtgaga accgagcaag aagcaaaaga tgccaaactg | 2340 |
| atgtcaaaga ggaatttagt tgagttggga ttagtttgga acacgaaaca agagtccaca | 2400 |

```
tccactgtgg atgatatcct agatagtatg cagccgcact ctaatgttag gagacttttc    2460
attgtaaatc atggtggtac aatcggtcct agttggttgt gcagcaacag caacatatac    2520
atgaaaaact tggagactct acatctagag agcgtatcgt gggctaacct tccacctatt    2580
gggcagttca atcacttaag aaagctaagg ctgagtaaaa ttgttgggat atcacagatt    2640
ggacctggct tcttcggtag cacgacagaa aaaagtgtct cacacttgaa ggcagttgag    2700
tttaatgata tgccagagct tgtcgagtgg gttgggggag ctagctggaa tatattctca    2760
gggattgaaa gaatcaagtg tactaattgt ccaaggctga cagggttgct gatatcagat    2820
tggtctattt cttctataga agacaacact gtatggttcc ctaatcttca tgacctttac    2880
attaatgaat gcccgaagtt gtgccttcct cccttgcctc acacttcaaa ggtatcccat    2940
attcgtatgg gagacttttc ttatgaaggt cgtaccatgt tggaaattaa taacccttct    3000
agatttgcct tcgaaaatct gggcgaccta gagaaattga tagttagcaa tgcactactc    3060
ttgtcattta tggatcttaa aaagctacat tccttgagac atatagaggt caatagatgc    3120
gaggaaacat ttttgagagg actggatgat ggtgttgtgc tacccacagt ccaatctctc    3180
aaacttggac aatttacacc taccaaaaag tctatgtcaa atttgttcaa atgtttccca    3240
gcactttctt ctttggatgt gatggcatca ctatcggatg aggaccacga ggaagtggta    3300
ctgcattttc caccctctag ctcgctgaga gatgtcacct tcaaagggtg taagaatctg    3360
atcctaccca tggaggaaga agctggattt tgtggcctct tgtcgctcga gtcagtgacc    3420
atacgcaaat gtgacaagct gttctctcgg tggtccatca caggacgagc agctcagact    3480
cagactcaga gcatcatcaa ccctctcccc cctacctga ggaaactctc cctttattat    3540
atggaaactc tgcctcagga agctctgctc gcgaatttga catctcttga gaaactcaca    3600
ctagataatt gtcttggttg tgagcaaagc accgagcgga tggctctgcc cgcgaatcta    3660
gcatctctta ccagtctaga gttagttgat tgcagaaata tcacaatgga tggattcgat    3720
cctcgcatca cattcagcct cgagagtcta agagtgtaca ataagagaaa acatgggact    3780
gatccgtatt ctgtagcagc agatctactt gtagcggtgg tgaggaccaa aacaatgccc    3840
gacgtttcct tcaaactggt gagcattgat gtggacagca tctcgggagt gcttgttgct    3900
cccatctgca ggctgctctc cgctacccte ggcgcgttaa agttcagaaa tgattggcgg    3960
acagagaact tcacaaaaga gcagaacgag gcgtttcagc tcctcacgtc tctcgtattc    4020
cttgagtttg ataattgcat ggctctccag tctctccccc aaggactgca tcgccatcct    4080
tctctcaagg taatacttat ctgggagcct caaaagatca tatccctgcc taaggagggc    4140
ctccccgatt cactacgagt actacaaata gtcactgtt gtgctgagct ttatgaggca    4200
tgccagcgat tgaagggaac aaggccagat atagaagtac ttgcccacaa agctgatgtg    4260
caaaattga                                                            4269
```

<210> SEQ ID NO 2
<211> LENGTH: 1422
<212> TYPE: PRT
<213> ORGANISM: Zea mays

<400> SEQUENCE: 2

```
Met Glu Val Ala Leu Gly Thr Ala Lys Ser Leu Leu Gly His Val Leu
1               5                   10                  15

Asn Ser Ile Ser Asp Asp Trp Met Lys Ser Tyr Val Ser Ser Ala Glu
            20                  25                  30
```

-continued

```
Leu Gly Thr Asn Leu Asn Met Ile Lys Glu Lys Met Arg Tyr Ala Arg
         35                  40                  45

Ala Leu Leu Asp Val Ala Lys Gly Arg Asp Asp Val Val Ala Gly Asn
 50                  55                  60

Pro Asn Leu Leu Glu Gln Leu Glu Thr Leu Gly Lys Lys Val Asp Glu
 65                  70                  75                  80

Ala Glu Asp Ala Val Asp Glu Leu His Tyr Phe Met Ile Gln Asp Lys
                 85                  90                  95

His Asp Gly Thr Arg Asp Ala Ala Pro Glu Leu Gly Gly Gly Leu Ala
            100                 105                 110

Ala Gln Ala His His Ala Arg His Ala Ala Arg His Thr Ala Gly Asn
        115                 120                 125

Trp Leu Ser Cys Phe Ser Gly Cys Cys Thr Arg Asp Asn Ala Ala Ala
    130                 135                 140

Thr Asp Ala Met Ser Gly Asp Gly Gly His Val Gly Lys Leu Ser Phe
145                 150                 155                 160

Asn Arg Val Ala Met Ser Asn Lys Ile Lys Leu Leu Ile Glu Glu Leu
                165                 170                 175

Gln Ser Asn Ser Thr Pro Val Ser Asp Leu Leu Lys Ile Val Ser Asp
            180                 185                 190

Thr Thr Asn Phe Ser Ser Thr Lys Arg Pro Pro Thr Ser Ser Gln
        195                 200                 205

Ile Thr Gln Asp Lys Leu Phe Gly Arg Asp Ala Ile Phe Lys Lys Thr
    210                 215                 220

Ile Asp Asp Ile Ile Ile Ala Lys Asp Ser Gly Lys Thr Leu Ser Val
225                 230                 235                 240

Leu Pro Ile Phe Gly Leu Gly Gly Ile Gly Lys Thr Thr Phe Thr Gln
                245                 250                 255

His Leu Tyr Asn His Thr Glu Phe Glu Lys Tyr Phe Thr Val Arg Val
            260                 265                 270

Trp Ile Cys Val Ser Thr Asn Phe Asp Val Leu Arg Leu Thr Lys Glu
        275                 280                 285

Ile Leu Ser Cys Leu Pro Ala Thr Glu Asn Ala Gly Asp Lys Ile Ala
    290                 295                 300

Asn Asp Thr Thr Asn Phe Asp Leu Leu Gln Lys Ser Ile Ala Glu Arg
305                 310                 315                 320

Leu Lys Ser Lys Arg Phe Leu Ile Val Leu Asp Asp Ile Trp Glu Cys
                325                 330                 335

Ser Asn Asn Glu Glu Trp Glu Lys Leu Val Ala Pro Phe Lys Lys Asn
            340                 345                 350

Asp Thr Ser Gly Asn Met Ile Leu Val Thr Thr Arg Phe Pro Lys Ile
        355                 360                 365

Val Asp Leu Val Lys Lys Glu Thr Asn Pro Val Asp Leu Arg Gly Leu
    370                 375                 380

Asp Pro Asp Glu Phe Trp Lys Phe Phe Gln Ile Cys Ala Phe Gly Ser
385                 390                 395                 400

Ile Gln Asp Val Glu His Gly Asp Gln Glu Leu Ile Gly Ile Ala Arg
                405                 410                 415

Gln Ile Ala Asp Lys Leu Lys Cys Ser Pro Leu Ala Ala Lys Thr Val
            420                 425                 430

Gly Arg Leu Leu Ile Lys Lys Pro Leu Gln Glu His Trp Met Lys Ile
        435                 440                 445

Leu Glu Asn Lys Gln Trp Leu Glu Glu Lys Asn Gly Asp Asp Ile Ile
```

```
            450             455             460
Pro Ala Leu Gln Ile Ser Tyr Asp Tyr Leu Pro Phe His Leu Lys Lys
465                 470                 475                 480

Cys Phe Ser Ser Phe Ala Leu Phe Pro Glu Asp Tyr Lys Phe Asp Lys
                485                 490                 495

Ser Glu Ile Ile Arg Leu Trp Asp Ser Ile Gly Ile Gly Ser Ser
            500                 505                 510

Ile Gln Gln Lys Lys Ile Glu Asp Ile Gly Ser Asn Tyr Phe Asp Glu
            515                 520                 525

Leu Leu Asp Ser Cys Phe Leu Ile Lys Gly Glu Asn Asp Phe Tyr Val
        530                 535                 540

Met His Asp Leu Ile Leu Asp Leu Ser Arg Thr Val Ser Lys Gln Asp
545                 550                 555                 560

Cys Ala Tyr Ile Asp Cys Ser Ser Phe Glu Ala Asn Asn Ile Pro Gln
                565                 570                 575

Ser Ile Arg Tyr Leu Ser Ile Ser Met His Asn His Cys Ala Gln Asn
            580                 585                 590

Phe Glu Glu Met Ala Lys Leu Lys Glu Arg Ile Asp Ile Lys Asn
        595                 600                 605

Leu Arg Gly Leu Met Ile Phe Gly Asn Tyr Ile Arg Leu Gln Leu Val
610                 615                 620

Asn Ile Leu Arg Asp Thr Phe Lys Glu Ile Arg Arg Leu Arg Val Leu
625                 630                 635                 640

Ser Ile Phe Ile Tyr Ser His Ser Ser Leu Pro Asn Asn Phe Ser Glu
                645                 650                 655

Leu Ile His Leu Arg Tyr Leu Lys Leu Asn Ser Pro Ser Tyr Leu Glu
            660                 665                 670

Ile Ser Leu Pro Asn Thr Ile Ser Arg Phe Tyr His Leu Lys Phe Leu
            675                 680                 685

Asp Leu Lys Gln Trp Gly Ser Asp Arg Ser Leu Pro Lys Asp Ile Ser
        690                 695                 700

Arg Leu Glu Asn Leu Arg His Phe Ile Ala Ser Lys Glu Phe His Thr
705                 710                 715                 720

Asn Val Pro Glu Val Gly Lys Met Lys Phe Leu Gln Glu Leu Lys Glu
                725                 730                 735

Phe His Val Lys Lys Glu Ser Val Gly Phe Glu Leu Gly Glu Leu Gly
                740                 745                 750

Lys Leu Ala Glu Leu Gly Gly Glu Leu Asn Ile Leu Gly Leu Glu Lys
            755                 760                 765

Val Arg Thr Glu Gln Glu Ala Lys Asp Ala Lys Leu Met Ser Lys Arg
            770                 775                 780

Asn Leu Val Glu Leu Gly Leu Val Trp Asn Thr Lys Gln Glu Ser Thr
785                 790                 795                 800

Ser Thr Val Asp Asp Ile Leu Asp Ser Met Gln Pro His Ser Asn Val
                805                 810                 815

Arg Arg Leu Phe Ile Val Asn His Gly Gly Thr Ile Gly Pro Ser Trp
                820                 825                 830

Leu Cys Ser Asn Ser Asn Ile Tyr Met Lys Asn Leu Glu Thr Leu His
            835                 840                 845

Leu Glu Ser Val Ser Trp Ala Asn Leu Pro Pro Ile Gly Gln Phe Asn
        850                 855                 860

His Leu Arg Lys Leu Arg Leu Ser Lys Ile Val Gly Ile Ser Gln Ile
865                 870                 875                 880
```

```
Gly Pro Gly Phe Phe Gly Ser Thr Thr Glu Lys Ser Val Ser His Leu
            885                 890                 895

Lys Ala Val Glu Phe Asn Asp Met Pro Glu Leu Val Glu Trp Val Gly
            900                 905                 910

Gly Ala Ser Trp Asn Ile Phe Ser Gly Ile Glu Arg Ile Lys Cys Thr
            915                 920                 925

Asn Cys Pro Arg Leu Thr Gly Leu Leu Ile Ser Asp Trp Ser Ile Ser
    930                 935                 940

Ser Ile Glu Asp Asn Thr Val Trp Phe Pro Asn Leu His Asp Leu Tyr
945                 950                 955                 960

Ile Asn Glu Cys Pro Lys Leu Cys Leu Pro Pro Leu Pro His Thr Ser
            965                 970                 975

Lys Val Ser His Ile Arg Met Gly Asp Phe Ser Tyr Glu Gly Arg Thr
            980                 985                 990

Met Leu Glu Ile Asn Asn Pro Ser Arg Phe Ala Phe Glu Asn Leu Gly
            995                 1000                1005

Asp Leu Glu Lys Leu Ile Val Ser Asn Ala Leu Leu Leu Ser Phe
        1010                1015                1020

Met Asp Leu Lys Lys Leu His Ser Leu Arg His Ile Glu Val Asn
    1025                1030                1035

Arg Cys Glu Glu Thr Phe Leu Arg Gly Leu Asp Asp Gly Val Val
    1040                1045                1050

Leu Pro Thr Val Gln Ser Leu Lys Leu Gly Gln Phe Thr Pro Thr
    1055                1060                1065

Lys Lys Ser Met Ser Asn Leu Phe Lys Cys Phe Pro Ala Leu Ser
    1070                1075                1080

Ser Leu Asp Val Met Ala Ser Leu Ser Asp Glu Asp His Glu Glu
    1085                1090                1095

Val Val Leu His Phe Pro Pro Ser Ser Ser Leu Arg Asp Val Thr
    1100                1105                1110

Phe Lys Gly Cys Lys Asn Leu Ile Leu Pro Met Glu Glu Glu Ala
    1115                1120                1125

Gly Phe Cys Gly Leu Leu Ser Leu Glu Ser Val Thr Ile Arg Lys
    1130                1135                1140

Cys Asp Lys Leu Phe Ser Arg Trp Ser Ile Thr Gly Arg Ala Ala
    1145                1150                1155

Gln Thr Gln Thr Gln Ser Ile Ile Asn Pro Leu Pro Pro Tyr Leu
    1160                1165                1170

Arg Lys Leu Ser Leu Tyr Tyr Met Glu Thr Leu Pro Gln Glu Ala
    1175                1180                1185

Leu Leu Ala Asn Leu Thr Ser Leu Glu Lys Leu Thr Leu Asp Asn
    1190                1195                1200

Cys Leu Gly Cys Glu Gln Ser Thr Glu Arg Met Ala Leu Pro Ala
    1205                1210                1215

Asn Leu Ala Ser Leu Thr Ser Leu Glu Leu Val Asp Cys Arg Asn
    1220                1225                1230

Ile Thr Met Asp Gly Phe Asp Pro Arg Ile Thr Phe Ser Leu Glu
    1235                1240                1245

Ser Leu Arg Val Tyr Asn Lys Arg Lys His Gly Thr Asp Pro Tyr
    1250                1255                1260

Ser Val Ala Ala Asp Leu Leu Val Ala Val Val Arg Thr Lys Thr
    1265                1270                1275
```

```
Met Pro Asp Val Ser Phe Lys Leu Val Ser Ile Asp Val Asp Ser
    1280            1285            1290

Ile Ser Gly Val Leu Val Ala Pro Ile Cys Arg Leu Leu Ser Ala
    1295            1300            1305

Thr Leu Gly Ala Leu Lys Phe Arg Asn Asp Trp Arg Thr Glu Asn
    1310            1315            1320

Phe Thr Lys Glu Gln Asn Glu Ala Phe Gln Leu Leu Thr Ser Leu
    1325            1330            1335

Val Phe Leu Glu Phe Asp Asn Cys Met Ala Leu Gln Ser Leu Pro
    1340            1345            1350

Gln Gly Leu His Arg His Pro Ser Leu Lys Val Ile Leu Ile Trp
    1355            1360            1365

Glu Pro Gln Lys Ile Ile Ser Leu Pro Lys Glu Gly Leu Pro Asp
    1370            1375            1380

Ser Leu Arg Val Leu Gln Ile Ser His Cys Cys Ala Glu Leu Tyr
    1385            1390            1395

Glu Ala Cys Gln Arg Leu Lys Gly Thr Arg Pro Asp Ile Glu Val
    1400            1405            1410

Leu Ala His Lys Ala Asp Val Gln Asn
    1415            1420

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aatcttcact cgagctgcaa                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gttgtacaat gtcgtcgtcg                                          20

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
gaaggtgacc aagttcatgc tgactgaaca gtgaagacga cgg                43

<210> SEQ ID NO 6
<211> LENGTH: 44
<212> TYPE: DNA
<213> ORGANISM: Artificial Sequence
<220> FEATURE:
<223> OTHER INFORMATION: Primer

<400> SEQUENCE: 6
gaaggtcgga gtcaacggat tggactgaac agtgaagacg acga               44
```

```
<210> SEQ ID NO 7
<211> LENGTH: 22
<212> TYPE: DNA
<213> ORGANISM: Artificial Sequence
<220> FEATURE:
<223> OTHER INFORMATION: Probe

<400> SEQUENCE: 7
ccaatcccca aaccctcgtc ga                                            22

<210> SEQ ID NO 8
<211> LENGTH: 41
<212> TYPE: DNA
<213> ORGANISM: Artificial Sequence
<220> FEATURE:
<223> OTHER INFORMATION: Primer

<400> SEQUENCE: 8
gaaggtgacc aagttcatgc tacaggttca acgtgcccac g                       41

<210> SEQ ID NO 9
<211> LENGTH: 41
<212> TYPE: DNA
<213> ORGANISM: Artificial Sequence
<220> FEATURE:
<223> OTHER INFORMATION: Primer

<400> SEQUENCE: 9
gaaggtcgga gtcaacggat tacaggttca acgtgcccac c                       41

<210> SEQ ID NO 10
<211> LENGTH: 23
<212> TYPE: DNA
<213> ORGANISM: Artificial Sequence
<220> FEATURE:
<223> OTHER INFORMATION: Probe

<400> SEQUENCE: 10
ctgacggagt agtcgacgtc gaa                                           23

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
gaaggtgacc aagttcatgc tcctgcctgc cactcctcg                          39

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
gaaggtcgga gtcaacggat tcctgcctgc cactcctcc                          39

<210> SEQ ID NO 13
<211> LENGTH: 19
<212> TYPE: DNA
<213> ORGANISM: Artificial Sequence
<220> FEATURE:
<223> OTHER INFORMATION: Probe
```

<400> SEQUENCE: 13
ggtggagcgg gagtccgga                                                    19

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctgctgatgt ctggaagaac cct                                               23

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agcatcatgc cagcaggttt t                                                 21

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
atctctccct cgctctcctt ctc                                               23

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agcagcaggt tggtcgaatg                                                   20

<210> SEQ ID NO 18
<211> LENGTH: 430
<212> TYPE: DNA
<213> ORGANISM: Artificial Sequence
<220> FEATURE:
<223> OTHER INFORMATION: Reference Sequence
<220> FEATURE:
<221> NAME/KEY: misc_feature
<222> LOCATION: (186)..(186)
<223> OTHER INFORMATION: n is a or t

<400> SEQUENCE: 18
aacatatgag ctattggcat gtgcactcga gaaggataat agagctgagg aagcacatag        60
aatctggcag aataaagtgg gccacgatct gcattcggtc ccttggcgtt tctgccgtct       120
tatgttggct atctactacc gaaacaatag gctagacagg ctcgtgaagg tttggacaca       180
gacccngtaa ctttatgatg cactttatat tttactttta catactttcc atttgataat       240
gtgccttaca tgaattactt tacctgcctc ttatgccgat ttagctcttc aaagaactcg       300
aagcttgtgg ccgtaaacct ccaagcaaag acattgtgcg gaaagtcgaa gatgcatacg       360
aaacgcttgg attactagaa gataaaaagg cgttgcttga taaatacaag gatttataca       420
acaaaccgtc                                                              430

<210> SEQ ID NO 19
<211> LENGTH: 401
<212> TYPE: DNA
<213> ORGANISM: Artificial Sequence
<220> FEATURE:
<223> OTHER INFORMATION: Reference Sequence
<220> FEATURE:
<221> NAME/KEY: misc_feature
<222> LOCATION: (201)..(201)
<223> OTHER INFORMATION: n is a or g

<400> SEQUENCE: 19
tgtcagatct tgctggatat tcaaatcata agcatcatta gccacagttt tggctccttt      60
ttcggagggc ttgtccacaa atgaaactct cttggatgtc aaagatttgt ttggttcttg     120 gatattttc acataaattt tgcggtcaac aagctgacag agaggttttg aaagctgctc      180
gtccattgag atttccactg ntctttttga tgattttgct tgacatgttt tctcgaattt     240
cctcttcctg tagtatgttt tttctttgag ttttgatgat ccgtctgcgc ttttaggtac     300
agcatttctc ctggtgtacc atgagcccaa gcacttgcta attgtatctg agaagagata     360
tgtccactct ctcacaacat tctcatgtag tttttgccga c                          401

<210> SEQ ID NO 20
<211> LENGTH: 43
<212> TYPE: DNA
<213> ORGANISM: Artificial Sequence
<220> FEATURE:
<223> OTHER INFORMATION: Primer

<400> SEQUENCE: 20
gaaggtgacc aagttcatgc tatatggcac gcctgttgat gaa                        43

<210> SEQ ID NO 21
<211> LENGTH: 43
<212> TYPE: DNA
<213> ORGANISM: Artificial Sequence
<220> FEATURE:
<223> OTHER INFORMATION: Primer

<400> SEQUENCE: 21
gaaggtcgga gtcaacggat tatatggcac gcctgttgat gag                        43

<210> SEQ ID NO 22
<211> LENGTH: 29
<212> TYPE: DNA
<213> ORGANISM: Artificial Sequence
<220> FEATURE:
<223> OTHER INFORMATION: Probe

<400> SEQUENCE: 22
taataacagt gtctgaagag acctcagat                                        29

<210> SEQ ID NO 23
<211> LENGTH: 46
<212> TYPE: DNA
<213> ORGANISM: Artificial Sequence
<220> FEATURE:
<223> OTHER INFORMATION: Primer

<400> SEQUENCE: 23
gaaggtgacc aagttcatgc taaagtactc atgactcacg agagca                     46

```
<210> SEQ ID NO 24
<211> LENGTH: 46
<212> TYPE: DNA
<213> ORGANISM: Artificial Sequence
<220> FEATURE:
<223> OTHER INFORMATION: Primer

<400> SEQUENCE: 24
gaaggtcgga gtcaacggat taaagtactc atgactcacg agagct           46

<210> SEQ ID NO 25
<211> LENGTH: 23
<212> TYPE: DNA
<213> ORGANISM: Artificial Sequence
<220> FEATURE:
<223> OTHER INFORMATION: Probe

<400> SEQUENCE: 25
ctggaaagtg ggaccacacg gat                                    23

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ggaagggaat ttgagccccc                                        20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgccagcctc aattcctctg                                        20
```